United States Patent [19]

Veber et al.

[11] 3,959,248

[45] May 25, 1976

[54] ANALOGS OF THYROTROPIN-RELEASING HORMONE

[75] Inventors: Daniel F. Veber, Ambler; Frederick W. Holly, Glenside; Ruth F. Nutt, Green Lane; Sandor L. Varga, Harleysville, all of Pa.

[73] Assignee: Merck & Co., Inc., Rahway, N.J.

[22] Filed: Jan. 27, 1975

[21] Appl. No.: 543,734

Related U.S. Application Data

[63] Continuation-in-part of Ser. No. 457,689, April 3, 1974, abandoned.

[52] U.S. Cl.......................... 260/112.5 TR; 424/177
[51] Int. Cl.$^2$................. C07C 103/52; A61K 37/00
[58] Field of Search.................. 260/112.5, 112.5 TR

[56] References Cited
UNITED STATES PATENTS 3,912,705  10/1975  Fujino et al................. 260/112.5 R

OTHER PUBLICATIONS

Inouye et al.: Bull. Chem. Soc. Japan, 44, 1689–1691 (1971).
Gillessen et al.: Helv. Chim. Acta, 53, 63–72 (1970).
Gillessen et al.: Helv. Chim. Acta, 54, 1335–1342 (1971).
Chang et al.: J. Med. Chem., 14, 484–487 (1971).
J. M. Stewart and J. D. Young, "Solid Phase Peptide Synthesis," Freeman and Co., San Francisco, 1969, pp. 1–26.
Beyerman et al.: Rec. Trav. Chim. Pays–Bas, 90, 355–357 (1971).
Boler et al.: J. Med. Chem., 14, 475–476 (1971).
Baugh et al.: Endocrin., 87, 1015–1021 (1970).
Rivier et al.: J. Med. Chem., 479–482 (1972).

*Primary Examiner*—Lewis Gotts
*Assistant Examiner*—Reginald J. Suyat
*Attorney, Agent, or Firm*—J. Jerome Behan; Daniel T. Szura; William H. Nicholson

[57] ABSTRACT

Novel tripeptides are disclosed. These tripeptides have anti-depressant activity and thyrotropin releasing hormone activity. Processes for preparing these tripeptides are also disclosed.

53 Claims, No Drawings

ANALOGS OF THYROTROPIN-RELEASING HORMONE

This application is a continuation-in-part of U.S. application Ser. No. 457,689, No. 457,689, filed Apr. 3, 1974, now abandoned.

BACKGROUND OF THE INVENTION

This invention is directed to certain tripeptides and use as anti-depressant and/or thyroid hormone release stimulants-and processes for their preparation.

The naturally occurring thyrotropin releasing hormone (TRH) is the tripeptide L-pyroglutamyl-L-histidyl-L-proline amide. Methods of synthesizing this peptide are known. Specific processes are described in U.S. Pat. Nos. 3,753,569; 3,746,697; 3,757,003, and 3,752,800. Analogs, derivatives and isomers of TRH are also disclosed in "Vitamins and Hormones, Advances in Research and Applications" volume 29 pg. 1–39, Academic Press, N.Y. and London (1971); "Chemistry and Biology of Peptides, Proceedings of the Third American Peptide Symposium" pg. 601–608, Ann Arbor Science Publishers Inc., Ann Arbor, Michigan (1972); Zh. Obshch, Khim 42 No. 2, pg. 483, February (1972); J. Med. Chem. 15, pg. 8, 219, 479 (1972); J. Med. Chem. 16, pg. 1137–1140 (1973); C.A. 75, 49547 w, 49548 x, 77268 z, 88942 r (1971); C. A. 74, 13401 m, (1971); and C. A. 73, 21767 c, 95001 v (1970). Besides its thyroid hormone release stimulating activity, TRH has also been found to have anti-depressant effect of substantially immediate onset. [Prage Jr., et al., *LANCET* pg. 999, Nov. 11, 1972; Plotnikoff, et al., *SCIENCE*, 178,417 (1972)].

Novel tripeptides have been prepared having antidepressant activity and thyrotropin hormone release activity of the TRH type.

DESCRIPTION OF THE PREFERRED EMBODIMENTS

An embodiment of the preset invention is tripeptide having the formula $$M_1 - M_2 - M_3 - E \qquad (1)$$

wherein
 a. $M_1$ is selected from the group consisting of kic, kpc, and pca.
 b. $M_2$ is selected from the group consisting of his and $N^{3im}$ substituted-his.
 c. $M_3$ is selected from the group consisting of L-pip, L-pro, and L-tca, and
 E is selected from the group consisting of —$NH_2$ and —OR wherein R is $C_1$-$C_{10}$ alkyl
such that (i) pca and L-pro do not occur together in said tripeptide when E is —$NH_2$ and (II) his and L-pro do not occur together in said tripeptide when E is —OR.

For the sake of brevity, amino acids are abbreviated herein as follows:

| Amino Acids | Abbreviation |
|---|---|
| histidine | his |
| pyroglutamic acid | pca |
| proline | pro |
| 2-ketoimidazolidine-5-carboxylic acid | kic |
| 2-ketopiperidine-6-carboxylic acid | kpc |
| thiazolidine-5-carboxylic acid | tca |
| 2-pyrrolecarboxylic acid | prl |
| L-2-piperidinecarboxylic acid | L-pip |
| 2-ketooxazolidine-4-carboxylic acid | koc |

The prefix L-, or D,L- is used to designate an individual amino acid stereoisomer, or stereoisomer mixtures, respectively. Where no prefix is used, the amino acid includes both the L-stereoisomer and D,L-mixtures. Thus, e.g. pca includes L-pca and D,L-pca mixtures, including racemic mixtures. In general, the more preferred tripeptides of Formula I are those in which $M_1$, $M_2$ and $M_3$ all have the L- configuration.

In addition to the amino acid abbreviations, following is a list of abbreviations which are used herein for other components, reactants, solvents, protecting groups etx., which are involved in peptide preparation.

| COMPOUNDS, BLOCKING GROUPS, SOLVENTS, ETC. | ABBREVIATION |
|---|---|
| benzyloxycarbonyl | Z |
| 2,4-dinitrophenyl | DNP |
| dicyclohexylcarbodiimide | DCCI |
| dimethylformamide | DMF |
| 1-hydroxybenzotriazole | HBT |
| tert-butyloxycarbonyl | BOC |
| trifluoroacetic acid | TFA |
| resins | ⓟ |
| azide | $N_3$ |

The present tripeptides encompass two general groups of compounds—the amides, where terminal group E in Formula I is —$NH_2$, and the esters, where the terminal group E is —OR. R, in the ester group is any suitable alkyl group. Preferred alkyl groups are those having one to ten carbon atoms. These include unsubstituted as well as substituted alkyls-linear, branched and cyclic alkyls. Examples of suitable preferred R groups are t-butyl, n-decyl, cyclohexyl, n-nonyl, 2,4-dimethyl-n-heptyl and the like; hydrocarbon alkyl groups are more preferred— and methyl is a most preferred R group.

One group of preferred tripeptides are those having the Formula I in which $M_1$ is kic or kpc. Examples of these tripeptides are:
 kpc-his-pro-$NH_2$
 kpc-his-tca-$OC_4H_9$
 kic-$N^{3im}$ substituted-his-pro-$OC_{10}H_{21}$
 D,L-kpc-his-tca-$NH_2$
 L-kic-his-pro-$NH_2$
 L-kpc-$N^{3im}$ substituted-his-pro-$OC(CH_3)_3$
 D,L-kic-L-his-tac-$OC_2H_5$
 D,L-kpc-D,L-his-L-pip-O-cyclohexyl
 L-kic-D,L-his-L-pip-$OC_9H_{19}$
and the like. More preferred tripeptides are those in which $M_1$ in the Formula I is a six membered, heterocyclic ring containing amino acid residue. Most preferred tripeptide is L-kpc-L-his-L-pro-$NH_2$, having the formula:

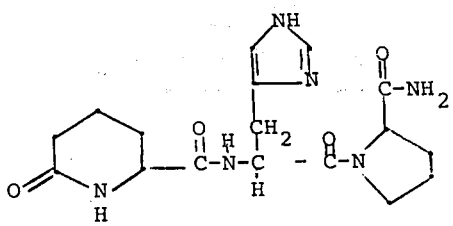

Another group of preferred tripeptides are those having Formula I in which $M_3$ is tca or L-pip. Examples of these preferred tripeptides are:

pca-$N^{3im}$ substituted-his-tca-$NH_2$
kic-his-L-pip-OCH($CH_3$)$_2$
kpc-L-his-L-pip-$NH_2$
kic-D,L-his-L-tac-O$C_2H_5$
D,Lpca-his-tca-O$C_5H_{18}$
kpc-his-L-pip-$NH_2$ and the like. More preferred tripeptides are pca-his-tca-E and pca-his-L-pip-E. Most preferred tripeptides are (1) L-pca-L-his-L-tca-E and (2) L-pca-L-his-L-pip-E having the formulae:

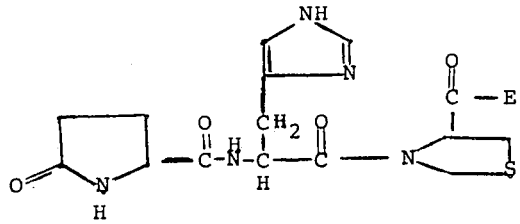

and

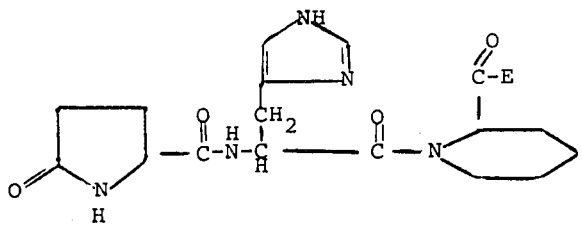

respectively.

Another group of preferred tripeptides are those having Formula I in which $M_2$ is $N^{3im}$ substituted his. $N^{3im}$ substituted indicates substitution on the histidine imidazoline N in the 3 position, as illustrated in the following formula

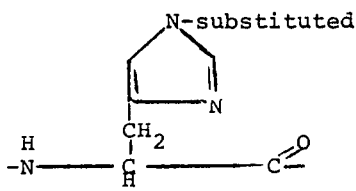

Preferred substituting groups are $C_1$-$C_6$ lower alkyl and —($CH_2$)$_b$COOH, where $b$ is an integer of from 1–4. Hydrocarbon alkyls e.g. —$CH_3$, t-butyl, cyclohexyl, and —$CH_2$COOH are more preferred substituting groups. Examples of preferred tripeptides having as $M_2$, $N^{3im}$-substituted-his are:

pca-$N^{3im}$-$C_5H_{11}$-his-L-tca-O-2-ethyl-n-hexyl
D,L-kpc-$N^{3im}$-$C_2H_5$-D,L-his-tca-$NH_2$
D,L-kic-$N^{3im}$-($CH_2$)$_4$-COOH-L-his-pro-O$C_{10}H_{21}$
koc-$N^{3im}$-($CH_2$)$_2$-COOH-L-his-L-pip-$NH_2$
L-pca-$N^{3im}$-CH($CH_3$)$_3$-his-pro-$NH_2$
kpc-$N^{3im}$-$C_3H_7$-his-L-pip-$NH_2$
L-kic-$N^{3im}$-cyclohexyl-D,L-his-tca-OCH($CH_3$)$_2$
kic-$N^{3im}$-($CH_2$)$_3$-COOH-his-L-pip-O-cyclopentyl and the like. The more preferred tripeptides of the group are exemplified by:

kpc-$N^{3im}$-$CH_3$-his-L-pro-$NH_2$
kic-$N^{3im}$-$CH_3$-his-tca-$NH_2$
koc-$N^{3im}$-$CH_2$-COOH-L-his-L-pip-$NH_2$
pca-$N^{3im}$-$CH_3$-his-L-tca-O$C_{10}H_{21}$
pca-$N^{3im}$-$CH_2$-COOH-his-L-pip-$NH_2$
kic-$N^{3im}$-$CH_3$-D,L-his-pro-O$C_2H_5$ and the like.

Another group of preferred tripeptides having Formula I are those in which $M_1$ is kpc and $M_3$ is tca or L-pip. Examples of these tripeptides are:

kpc-his-tca-$NH_2$
kpc-$N^{3im}$-($CH_2$)$_2$-COOH-his-L-tca-$NH_2$
kpc-$N^{3im}$-cyclohexyl-L-his-L-pip-$NH_2$
kpc-D,L-his-tca-O$C_3H_7$
L-kpc-C,L-his-L-pip-O$C_{10}H_{21}$
D,L-kpc-$N^{3im}$-CH($CH_3$)$_3$-L-pip-O-cyclopentyl and the like. Most preferred peptides of this group are L-kpc-L-his-L-pip-E having the formula:

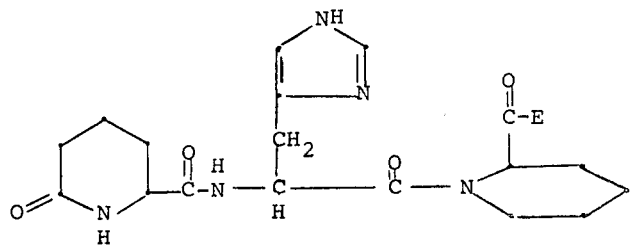

Another group of preferred tripeptides are those having the formula $M_4$—$M_2$—$M_3$—$NH_2$ wherein $M_4$ is selected from koc and prl and $M_2$ and $M_3$ are as defined above. Examples of these tripeptides are:

koc-his-pro-$NH_2$
prl-$N^{3im}$ substituted-his-tca-$NH_2$
koc-L-his-L-pip-$NH_2$
prl-D,L-his-pro-$NH_2$
L-prl-L-his-L-pro-$NH_2$
D,L-koc-his-pro-$NH_2$
D,L-prl-his-L-pip-$NH_2$
L-koc-$N^{3im}$ substituted-L-tca-$NH_2$ and the like.

Another embodiment of this invention are tripeptides having the formula pca-$N^{3im}$-$R^1$-his-pro-$NH_2$ wherein $R^1$ is —$(CH_2)_b$-COOH, $b$ being an integer from 1–4. Preferred $R^1$ is —$CH_2COOH$. Examples of these tripeptides are pca-$N^{3im}$-$(CH_2)_4$-COOH-his-pro-$NH_2$
pca-$N^{3im}$-$CH_2$-COOH-L-D,L-his-pro-$NH_2$
D,L-pca-$N^{3im}$-$(CH_2)_2$-COOH-L-his-L-pro-$NH_2$
D,L-pca-$N^{3im}$-$CH_2$-COOH-D,L-his-pro-$NH_2$ and the like. A most preferred tripeptide of Formula II is L-pca-$N^{3im}$-$CH_2$-COOH-L-his-L-pro-$NH_2$.

Another embodiment of this invention are tripeptides having the formula pca-$N^{3im}$-$R^2$-his-pro-OR wherein $R^2$ is $C_1$-$C_6$ lower alkyl, preferably hydrocarbon alkyl e.g. —$C_2H_5$, cyclohexyl, —$C(CH_3)_3$ and the like, or —$(CH_2)_b$ COOH where $b$ is an integer of from 1–4; and R is as defined above for formula I. Most preferred $R^2$ is —$CH_3$ and —$CH_2$—COOH. Examples of tripeptides of formula II are:

pca-$N^{3im}$-$C_2H_5$-his-pro-$OC_{10}H_{21}$
pca-$N^{3im}$-$C_6H_{13}$-his-pro-$OC_4H_9$
pca-$N^{3im}$-$CH(CH_3)_2$-his-pro-O-cyclohexyl
pca-$N^{3im}$-$(CH_2)_4$-COOH-his-pro-$OC_7H_{15}$
pca-$N^{3im}$-$CH_2$-COOH-his-pro-$OC(CH_3)_3$
D,L-pca-$N^{3im}$-$C_3H_7$-D,L-his-L-pro-$OC_4H_9$ and the like; and most preferred tripeptides are L-pca-$N^{3im}$-$CH_3$-L-his-L-pro-$OCH_3$ and L-pac-$N^{3im}$-$CH_2$-COOH-L-his-L-pro-$OCH_3$ In addition to the tripeptides described, salts of these tripeptides are also an embodiment of the present invention. These salts include pharmaceutically acceptable salts of inorganic acids, e.g. HCl, $H_2SO_4$, HBr, $H_3PO_4$ and the like, as well as organic acids, e.g. cyclohexylcarboxylic acid, tartaric acid, oxalic acid, fumaric acid, citric acid, malic acid, ascorbic acid, acetic acid, lactic acid, fatty acids, e.g. oleic, pamoic, palmitic and the like. By pharmaceutically acceptable, we mean that the salts are substantially non-toxic and have pharmacological activity like the tripeptide.

The tripeptides of the present invention can be prepared using various processes and techniques. The preparation generally involves coupling of appropriate amino acid components via the peptide linkage, $$-\overset{O}{\overset{\|}{C}}-\overset{H}{\underset{}{N}}-.$$

Where the peptide prepared is linear, coupling involves reaction between an α-amino group and a carboxyl group of different amino acid components. The general practice in controlling and directing this coupling is to protect or block, in the amino acid components, the functional groups which are not intended to take part in peptide bond formation. Important functional requirements of the blocking groups are that (1) they should not adversely affect the coupling reaction and (2) they should be conveniently removable as required during the peptide preparation.

Various types of blocking or protecting groups are available and may be used. Suitable amino protecting groups include acyl type groups having the formulae $$R^a-\overset{O}{\overset{\|}{C}},$$

R-$SO_2$—, $R^a$—S—, $(R^aO)_2$—P—O— where $R^a$ is alkyl, aryl, aralkyl, arkaryl, or substituted alkyl or aryl; urethane type groups having the formula $$R^b-O-\overset{O}{\overset{\|}{C}}- \text{ and } R^b-S-\overset{O}{\overset{\|}{C}}-$$

where $R^b$ is alkyl, aryl, alkaryl, aralkyl substituted alkyl or aryl, alkylamino, heterocyclic, and the like; alkyl, aryl and substituted alkyl or aryl groups; and arylidene groups having the formula $$R^c=\overset{H}{\underset{}{C}}-$$

where $R^c$ is an aryl or substituted aryl group.

Representative examples of the acyl type groups are formyl, p-toluenesulfonyl, chloroacetyl, trifluoroacetyl, phthaloyl, phosphoryl, benzenesulfonyl, o-nitrophenoxyacetyl, o-nitrophenylsulfenyl, dibenzylphosphoryl, and the like. Examples of alkyl and aryl blocking groups are triphenylmethyl, benzyl, trialkylsilyl, benzylthiomethyl, dinitrophenyl, diphenyl and the like. Useful arylidene groups are exemplified by benzylidene, 2-hydroxy-5-chlorobenzylidene and the like.

Most useful of the amino blocking groups are those of the urethane type having the formula $$R^b-O-\overset{O}{\overset{\|}{C}}-.$$

Examples of the especially useful urethane type protecting groups are those in which $R^b$ is benzyl, substituted benzyl, e.g. p-methoxybenzyl, p-nitrobenzyl, p-phenylazobenzyl, p-bromobenzyl, 2-nitrobenzyl and the like, cycloalkyl, e.g. methylcyclohexyl, cyclopentyl, and the like, substituted cycloalkyl e.g. methylcyclohexyl, dodecylcyclohexyl, isobtyl cyclopentyl and the like, adamantyl, piperidino, dimethylamino and alkyl groups e.g, n-propyl, t-butyl, t-amyl, octyl, dodecyl, and the like.

In addition to the blocking groups described above, the amino function can also be protected by salt formation provided the amino group is sufficiently basic.

Carboxyl group protection of the amino acid component is generally effected by esterification, amide or hydrazide formation and salt formation.

Useful carboxyl protecting esters include alkyl esters such as methyl, ethyl, t-butyl, decyl and the like, aryl esters such as benzyl, phenyl, benzhydryl, and the like, substituted alkyl esters, and substituted phenyl esters such as pentamethylbenzyl, phenylazophenyl, o-cyanobenzyl and the like.

Hydrazides which are useful carboxyl protecting groups are, in general, substituted hydrazides. Examples of such hydrazides are benzyloxyhydrazide, tertbutyloxycarbonylhydrazide, phenylhydrazide, tritylhydrazide, and the like.

Protection of the carboxyl group by forming an amide is of little general use since the amide group is difficult to remove without disrupting the peptide bond itself. However, where, as here, the tripeptide end group may be an amide, this means of carboxyl protection can be advantageously used.

In the case of some of the ester carboxyl protecting groups, these groups also have what is known as an activating effect. This activation refers to enhancement of the coupling reactivity. The extent of the activation is dependent on the particular ester chemical configuration, the general rule being that activation is determined by the extent to which the protecting group makes the carboxyl function more susceptible to nucleophilic attack. Examples of carboxyl activating ester groups are p-nitrophenyl, 1,4-dinitrophenyl, N-hydroxysuccinimidyl, perfluorophenyl, cyanomethyl, perclorophenyl, 2,4,5-trichlorophenyl, 4-methylthiophenyl, 8-hydroxybenzotriazole, thioester, e.g. p-nitrobenzylthio, p-nitrophenylthio, phenylthio and the like.

Coupling of the amino acid components can be accomplished by various reactions. Among reactions are included:

a. direct condensation of $N^\alpha$-blocked amino acid component with carboxyl blocked amino acid component.
b. conversion of $N^\alpha$ blocked amino acid component to the azide followed by reaction with a carboxyl blocked amino acid component,
c. reaction of $N^\alpha$ blocked amino acid halide or mixed anhydride with carboxyl blocked amino acid component,
d. reaction of $N^\alpha$-blocked amino acid active ester, with carboxyl blocked amino acid,
e. direct coupling of $N^\alpha$-blocked amino acid component with carboxyl blocked amino acid component using a coupling agent, e.g. a carbodiimide; a carbodiimide plus a hydroxybenzotriazole; a carbodiimide plus N-hydroxysuccinimide; triphenylphosphite plus imidazole; triphenylphosphine plus dipyridyl-2,2'disulfide; or Woodward's reagent.

Of the coupling reactions, especially useful are the azide method (b) and method (e) using a carbodiimide.

Various preparative schemes can be used for obtaining the present peptides. A convenient scheme utilizes sequential coupling of individual amino acids to prepare first a dipeptide intermediate and then the final tripeptide.

In carrying out the coupling steps, the component reacting at its carboxyl group is generally protected at its alpha amino group while the component reacting at its alpha amino group is generally protected at its carboxyl group. Where the component also has a secondary functional group, e.g. the imidazole group in histidine, it may also be protected. The following equations illustrate such a stepwise sequence. The sequence shows an amide preparation— analogous sequence is used to prepare the ester tripeptides, Y, in the equations, is a carboxyl protecting group.

(a) L-pca + L-his—Y— $\xrightarrow{\text{(couple)}}$ L-pca-L-his—Y (b) L-pca-L-his—Y $\xrightarrow{(-Y)}$ L-pca-L-his (c) L-pca-L-his + L-tca—NH$_2$ $\xrightarrow{\text{(couple)}}$ -continued L-pca-L-his-L-tca—NH$_2$ If Y in step (a) is an activating group, steps (b) and (c) may be combined. Also, although L-pca is not shown to be protected at its amino group, it may be protected if desired. In that case, an additional step would be required to remove the protecting group to yield the L-pca-L-his-L-tca-NH$_2$.

The reaction sequence shown in the equations (a) through (c) is illustrative and not meant to be limiting. Thus, the sequence used may involve coupling M$_2$ amino acid with M$_3$—NH$_2$ (or OR) amino acid component to produce the M$_2$ M$_3$—NH$_2$ (or OR) dipeptide which in turn is coupled with the M$_1$ amino acid to produce the desired M$_1$—M$_2$—M$_3$—NH$_2$ (or OR) tripeptide.

Another scheme for preparing the present tripeptides utilizes a resin matrix on which the peptide is sequentially built. This scheme may involve a soluble resin system or an insoluble system. The insoluble resin system is preferred and is conventionally referred to as solid phase (or Merrifield) synthesis. The insoluble resin is generally one that has sites at which carboxyl groups can be found. An example of such a resin is one commonly referred to as Merrifield resin. One form of this resin is a copolymer of styrene and divinylbenzene which is chloromethylated to provide carboxyl reactive sites. The peptide is built up one amino acid at a time until the desired tripeptide is formed. The tripeptide is then freed from the resin.

This procedure is illustrated in the reaction equation sequence set out below. In the equations, ⓟ is used to describe the resin and X and X$^1$ represent amino blocking groups.

(i) X-L-pip + ⓟ → X-L-pip-ⓟ

(ii) X-L-pip-ⓟ $\xrightarrow{(-X)}$ L-pip-ⓟ

(iii) X$^1$-L-his + L-pip-ⓟ $\xrightarrow{\text{(couple)}}$ X$^1$-L-his-L-pip-ⓟ

(iv) X$^1$-L-his-L-pip-ⓟ $\xrightarrow{(-X^1)}$ L-his-L-pip-ⓟ

(v) L-kic + L-his-L-pip-ⓟ → L-kic-L-his-L-pipⓟ

The next step (or steps) in the sequence involves freeing the tripeptide from the resin ⓟ. Depending on the reaction system used, the freed tripeptide may have an acid, ester or amide terminal group. Where, after the resin is cleaved and the terminal group is the acid, this tripeptide can be converted to the crresponding ester or amid by conventional procedures. Similarly, where the freed tripeptide has an ester terminal group, the amide group may, if desired, be substituted therefore by conventional procedures.

A most convenient method for separating the tripeptide from the resin ⓟ is by transesterifying with a suitable alcohol. One advantage of this method is that ester is obtained directly and the ester can be readily converted to the amide if desired. These reactions are illustrated below:

TRIPEPTIDE ESTER

L-kic-L-his-L-pip-+ ROH → L-kic-L-his-L-pip-OR

TRIPEPTIDE AMIDE

L-kic-L-his-L-pip-OR + $NH_3$ → L-kic-L-his-L-pip-$NH_2$

Although not shown in the above reaction equation, the nitrogens in the kic and the histidine imidazole group can be blocked during the reaction if desired, with the blocking groups being removed at an appropriate point in the peptide preparation. $N^{3im}$-substituted-his- containing tripeptides can also be prepared using solid phase synthesis, with the substituting group being added either before or during the course of the synthesis.

In both schemes described bove and in peptide preparation generally, the blocking and/or activating groups are added and removed. Both removal and addition of blocking groups is accomplished using techniques and reaction systems known and available to those skilled in the peptide art. Examples of some reactions by which the protecting or blocking groups are removed are reduction with sodium in liquid $NH_3$, hydrogenolysis (e.g. using Pd/$^C$ as a catalyst) treatment with hydrohalo acid (HCl, HBr etc.) in acetic acid, or treatment with TFA. The particular reaction system used to deblock, that is to remove a blocking group, as well as to block a group in an amino acid component is chosen so that, (1) if necessary, removal of blocking groups is selective and (2) it does not adversely affect the peptide preparation process.

Following are examples illustrating the preparation of tripeptides of Formula I and some intermediates. All parts are by weight unless otherwise indicated.

EXAMPLE 1

A. Preparation of L-2-ketoimidazolidine-5-carboxylic acid

A solution of 25 grams (g) of NaOH in 760 milliliters (ml) of water was prepared in a vessel and placed in a cooling bath. Five ml of bromine were added to the solution with stirring. When the temperature of this mixture reached about 0°C., 26.6g. of $N^\alpha$ -benzyloxycarbonyl asparagine was dissolved in the mixture. The solution was then warmed to 75°C. and kept at this temperature for 45 minutes. The solution was then cooled and extracted twice with 150 mls. of methylene chloride each time. The extracted solution was evaporated to dryness and the solid remaining was dried overnight in a vacuum oven. The dried solid was extracted with ethanol. The extract was evaporated to the point where the product L-2-ketoimidazolidine-5-carboxylic acid,

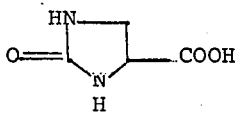

precipitated.

After filtration of the product, it was dried under vacuum. About 4.20 grams of acid product was obtained. The melting point was 166°–170°C. Elemental analysis of the product showed C=34.87% (theo.C=36.93%), H=4.52% (theo. H=4.65%) and N=19.5% (theo. N=21.53%).

B. Preparation of L-2-ketoimidazolidine-5-carbonyl-L-histidyl-L-proline-$OCH_3$ 19.8g (6.36 millimoles [mm] $N^\alpha$ tert-butyloxycabonyl-$N^{3im}$ 2,4-dinitrophenyl-L-histidyl-L-proline-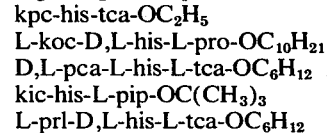, 2.0 equivalents of L-2-ketoimidazolidine-5-carboxylic acid, 2.0 equivalents of dicyclohexylcarbodiimide and 1.3 grams of 1-hydroxybenzotriazole were mixed in DMF and allowed to react at room temperature (R.T.) for about 5 hours. At the end of this time, reaction was substantially complete and the yield of L-kic-$N^{im3}$-DNP-L-his-L-pro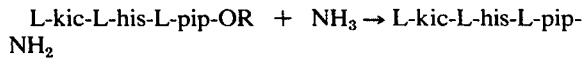was 98%. The dinitrophenyl blocking group was removed with $HSC_2H_4OH$/DMF and the product L-kic-L-his-L-pro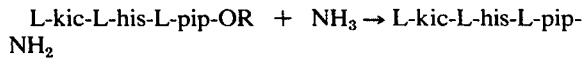 was washed with acetic acid, methanol and $CH_2Cl_2$.

The washed L-kic-L-his-L-pro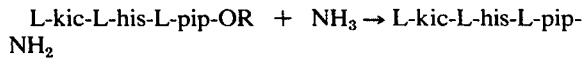(4.7g) was added to 188 ml. of methanol and 47.1 ml. triethylamine. This mixture was stirred at R.T. for 5 days and then allowed to stand at R.T. for about 6 days. The mixture was then filtered, evaporated to dryness and purified by elution through silica column (ration 200:1). The eluent was a mixture of 70 parts by volume $CHCl_3$, 30 parts by volume $CH_3OH$ and 3 parts by volume $H_2O$. The product L-kic-L-his-L-pro-$OCH_3$ was isolated by lyophilization. Yield was 1.54 grams.

C. Preparation of L-2-ketoimidazolidine-5-carbonyl-L-histidyl-L-proline-amide 0.8 grams of L-kic-L-his-L-pro-$OCH_3$ was added to about 10 ml. of liquid $NH_3$ and kept at R.T. for 7 days. This reaction mixture was dissolved in methanol. After evaporation in vacuo the residue faw freeze dried. The primary product obtained was L-kic-L-his-L-pro-$NH_2$.

EXAMPLE 2

Preparation of D,L-2-ketopiperidine-6-carbonyl-L-histidyl-L-proline-$OCH_3$; -$NH_2$ By substituting D,L-2-ketopiperidine-6-carboxylic acid for L-2-ketoimidazolidine-5-carboxylic acid and using substantially the same procedures as in Example 1B and 1C, the tripeptides, D,L-kpc-L-his-L-pro-$OCH_3$ and D, L-kpc-L-his-L-pro-$NH_2$ were prepared.

Examples of other tripeptides which are prepared using the general procedure of Example 1B are:
kpc-his-tca-$OC_2H_5$
L-koc-D,L-his-L-pro-$OC_{10}H_{21}$
D,L-pca-L-his-L-tca-$OC_6H_{12}$
kic-his-L-pip-$OC(CH_3)_3$
L-prl-D,L-his-L-tca-$OC_6H_{12}$
and the like, and these esters are converted to the corresponding amides using the procedure of Example 1C.

EXAMPLE 3

A. Preparation of L-pyroglutamyl-L-histidine-$OCH_3$

A vessel, equipped for agitation and cooling, was charged with L-histidine methyl ester dihydrochloride (72.9 g.) and L-pyroglutamic acid (39.1 g.) and acetonitrile (1200 ml). This mixture was cooled to 0°C. with stirring. Triethylamine (84 ml.) was added gradually over a 10 minute period, maintaining the temperature at 0°C. This mixture was then aged for 15 minutes. A solution of 76.5 g. of dicyclohexylcarbodiimide in 180 ml. of acetonitrile was then added gradually over a 5–10 minute period. The resulting mixture was aged at 0°C. for 30 minutes, was allowed to warm to room temperature, and was then stirred for 24 hours at room temperature.

The mixture was then filtered and the filter cake was washed 3 times with acetonitrile (100 ml. each time). This filtrate was discarded.

The washed cake was then slurried in the funnel four (4) times with methanol (150 ml. each time). This filtrate was evaporated under vacuum to a volume of 300 ml. and then 1200 ml. of diethyl ether was added slowly with stirring. This mixture was allowed to stand overnight (30 minutes aging is adequate) and then was filtered. The filter cake was washed twice with a 9 volume: 1 volume, diethylether: methanol mixture (75 ml. each time). This washed filter cake was then slurried with 500 ml. of chloroform for 2 hours. The slurry was filtered and the filter cake was washed four times with chloroform (45 ml. each time).

This washed cake (42.1 grams) was added to 168 ml. of methanol and heated rapidly to boiling. This hot mixture was filtered. The filtrate was allowed to cool to room temperature and was aged at room temperature for 3 hours. White crystalline product L-pyroglutamyl-L-histidine-$OCH_3$ was formed. This was filtered off and washed with 10 ml. of methanol. This washed material was dried. The yield of L-pyroglutamyl-L-histidine-$OCH_3$ was 24.1 g (28.7%). The product m.p. was 208°–210°C. Thin layer chromatographic (TLC) analysis showed the product to be 99% pure.

B. Preparation of L-pyroglutamyl-L-histidine hydrazide

In a vessel fitted with thermometer and stirrer and placed in an ice bath, 33.6 g. of L-pyroglutamyl-L-histidine-$OCH_3$ was dissolved in 640 ml. of methanol. When the solution temperature reached 10°C., 400 ml. of 97+% anhydrous hydrazine was added gradually over 5 minutes, maintaining the temperature below 20°C. The reaction mixture was stirred an additional 6 minutes at 18°–20°C., and then it was transferred to a second vessel and stripped under vacuum.

The resulting white solid was redispersed in 1040 ml. of ethanol-2BA (benzene denatured-absolute) and then the resulting mixture was stripped of ethanol. This redispersion/stripping step was repeated a second time.

The resulting white solid was next dispersed in 800 ml. of DMF. This dispersion was then evaporated under vacuum to a weight of 230 g. This evaporated material was dispersed in 800 ml. of ethanol-2BA, aged for 45 minutes at room temperature and filtered. The filter cake was washed twice, with ethanol-2BA (80 ml. each time) and dried. This dried product was dispersed in 3200 ml. of methanol and heated to boiling. The mixture was allowed to cool to room temperature, with stirring, filtered and the filter cake was washed twice with methanol (60 ml. each time). The product was dried under vacuum. Yield of L-pyroglutamyl-L-histidine-hydrazide was 25.69 g. (76.5%). TLC analysis showed this product to be substantially pure.

C. Preparation of L-pyroglutamyl-L-histidyl-L-thiazolidine-5-carboxylic acid amide 800 mg. (3mm) of L-pyroglutamyl-L-histidine hydrazide was suspended in 80 ml. DMF. The suspension was cooled to −20°C. and brought to a pH of 1.5 by addition of 5.9M HCL in THF.

4ml. of 10% isoamylnitrite in DMF was added. The mixture was stirred for 25 minutes while keeping the temperature at −20°C. Then, 500 mg. (3mm) of L-thiazolidine-5-carboxylic acid was added and the pH was adjusted to 8.5 by addition of 4.1 ml. triethylamine. The mixture was stored at −15°C. for 7 days.

DMF was then removed in vacuo. The residue was dissolved in 40 ml. of 0.4M carbonate-bicarbonate buffer (pH=10) and the solution was extracted four times with a mixture of 30 ml. n-butanol/40 ml. chloroform.

The aqueous layer was evaporated and the residue was extracted with 50, 25 and 25 ml. of methanol. The methanol solutions were combined and evaporated in vacuo. The residue remaining is L-pyroglutamyl-L-histidyl-l-thiazolidine-5-carboxylic acid.

The L-pyroglutamyl-L-histidyl-L-thiazolidine-5-carboxylic acid (615 mg.; 1.5 mm) was dissolved in 30 ml. DMF. 260 mg. (1.7 mm) of HBT was added to the solution and the pH adjusted to 4 with triethylamine. 180 mg. (3.4 mm) of $NH_4Cl$ was added followed by 385 mg. (1.7 mm + 10% excess) of DCCI. The reaction mixture was stirred overnight at R.T.

The reaction mixture was then filtered. The filtrate was evaporated, the residue was dissolved in 20 ml. of eluent (80:20:2 — chloroform:methanol:water) and charged to a 200 g. silica gel column.

The fractions containing the product L-pyroglutamyl-L-histidyl-L-thiazolidine-carboxylic acid amide, were pooled and evaporated; yield was 370 mg. of the product-substantially pure by TLC.

Other tripeptides which can be prepared using the general procedure of Example 3 are:

L-kic-L-his-L-pro-$NH_2$
D,L-kpc-his-L-pip-$NH_2$
pca-his-L-pip-$NH_2$
L-kpc-his-L-pip-$NH_2$
kic-his-tca-$NH_2$
koc-D,L-his-L-tca-$NH_2$
L-prl-L-his-L-pro-$NH_2$ and the like.

EXAMPLE 4

Preparation of L-pyroglutamyl-$N^{3im}$-carboxymethyl-L-histidyl-L-proline amide L-pca-L-his-L-pro-$NH_2$ is added to a DMF solution containing 1.1 equivalents of mono iodoacetic acid. The reaction mixture is stirred for about 18 hours and the solution is evaporated to dryness. The dried residue is chromatographed on a suitable, dry silica gel column using a mixture of $CHCl_3$: $CH_3OH$:$H_2O$ (50:40:10 by volume) as eluent, taking 5 ml. cuts. The fractions containing first major product eluted contain substantially pure L-pca-$N^{3im}$-$CH_2COOH$-L-his-L-pro-$NH_2$. Other products in the reaction mixture are L-pca-$N^{1im}$, $N^{3im}$-di-$CH_2COOH$-L-his-L-pro-$NH_2$ and L-pca-$N^{1im}$-$CH_2COOH$-L-his-L-pro-$NH_2$.

In some cases, the $N^{3im}$ substituted L-his containing product may be eluted as an iodide salt. This salt can be neutralized e.g. with Dowex 1 (hydroxide), to obtain the free tripeptide product.

Other $N^{3im}$ substituted-his containing tripeptides which are prepared from the appropriate tripeptide using the general procedure of Example 4 are:

N-pca-$N^{3im}$-n-hexyl-D,L-his-pro-$OCH_3$
D,L-pca-$N^{3im}$-$(CH_2)_4$-COOH-L-his-L-pro-$NH_2$ L-N$^{3im}$-isopropyl-D,L-his-L-pro-OC$_5$H$_{11}$
kic-N$^{3im}$-(CH$_2$)$_2$-COOH-his-L-tca-NH$_2$
D,L-kpc-N$^{3im}$-C$_2$H$_5$-his-L-pip-OC$_2$-H$_5$
L-kic-N$^{3im}$-CH$_2$COOH-L-his-L-pro-OCH$_3$
pca-N$^{3im}$-cyclohexyl-D,L-his-tca-NH$_2$
and the like.

EXAMPLE 5

Preparation of
L-proglutamyl-histidyl-L-piperidine-2-carboxylic acid methyl ester 1.5g. of L-pca-L-his-NH-NH$_2$ was dispersed in 40 ml. of DMF and cooled to −30°C. with stirring. To this dispersion was added 4.08 ml. of 5.25 M HCl in THF. Then, in a period of about 40 minutes, 0.77 ml. of isoamyl nitrite was added (0.65 ml. initial charge followed, by three increments of 0.051 ml, 0.035 ml, and 0.035 ml). To this mixture was added 965 mg (5.37 mm) L-piperidine-2-carboxylic acid methyl ester.HCl. Next about 4.1 ml. of triethylamine was added. The reaction mixture was then maintained at +5°C. for 96 hours and then at R.T. overnight. [During this period three additional increments (0.2 ml, 0.4 ml and 0.2 ml) of triethylamine were added to maintain pH at about 7.2].

At the end of this time, the triethylamine .HCl was filtered off. This residue was washed with DMF/diethyl ether (125 ml/50–75 ml). The wash was combined with the filtrate. This filter/wash procedure was repeated two more times. The final filtrate and washings were then evaporated in vacuo to yield 2.87 g. of crude tripeptide product. This crude product was purified by elution through silica gel column with 90/10/1-chloroform/methanol/water mixture. Products recovered were L-pca-L-his-L-pip-OCH$_3$ (787 mg) and L-pca-D,L-his-L-pip-OCH$_3$ (671 mg).

Substituting L-pip-NH$_2$ for L-pip-OCH$_3$ in Example 5, the analogous L-pca-his-L-pip-NH$_2$ is prepared.

Other tripeptides which are prepared using the general procedure of Example 5 are:
L-pca-his-L-tca-OCH$_3$
L-kpc-his-L-pip-OCH$_3$
L-pca-his-L-tca-NH$_2$
L-kic-his-L-pip-OC$_4$H$_9$
L-koc-his-L-pro-NH$_2$
L-prl-his-L-pro-NH$_2$
K-kic-his-L-pip-OC$_{10}$H$_{21}$
L-kpc-his-L-tca-OCH(CH$_3$)$_2$
and the like.

In addition to the methods of preparation illustrated by the examples and disclosed above, the present tripeptides may also be prepared using methods for preparing tripeptides of the TRH type disclosed in the art cited above. To the extent the disclosure in the art is required, it is incorporated herein by reference.

The tripeptides of the present invention are found to have anti-depressant activity and thyrotropin releasing hormone activity. Their activity as anti-depressants is as central nervous system (CNS) stimulants and was determined by testing representative tripeptides of the present invention using in vivo assay based on restoration of anti-convulsant action of methazolamide in picolinic acid treated mice. The thyrotropin releasing hormone activity of the present tripeptides was determined using the in vivo assay substantially as described in "Vitamins and Hormone" R.S. Harris et al, 29, 3–4 (1971).

In some cases, unlike TRH, the present tripeptides showed a separation of activity e.g. they had greater anti-depressant activity than thyrotropin releasing hormone activity. This type of separated activity would offer the advantage of making the tripeptide especially useful at proper dosages for treating depression without causing significant thyrotropin release when not desired or necessary.

The following table contains activity data for a number of representative peptides of the present invention. The protocols used to obtain the data were those described above. The results are expressed numerically as multiples of the TS (thyrotropin stimulation) and AD (anti-depressant) activity compared to the control TS and AD activities of TRH which have the value 1. The designation S.N. is used to indicate substantially no detectable activity at the dosage level tested.

TABLE I

| No | THYROTROPIN RELEASING HORMONE AND ANTI-DEPRESSANT ACTIVITIES Peptide | TS | AD |
|---|---|---|---|
| Control | TRH | 1 | 1 |
| 1 | L-2-ketopiperidine-6-carbonyl-L-histidyl-L-thiazolidine-5-carboxamide | 1 | 8 |
| 2 | L-2-ketopiperidine-6-carbonyl-L-histidyl-L-proline amide | 1 | 4 |
| 3 | D,L-2-ketopiperidine-6-carbonyl-L-histidyl-L-proline amide | 0.2 | 3 |
| 4 | L-pyroglutamyl-D,L-histidyl-L-thiazolidine-5-carboxamide | 0.2 | 2 |
| 5 | L-pyroglutamyl-L-histidyl-L-2-piperidine-carboxylic acid methyl ester | 0.2 | 1 |
| 6 | L-2-ketoimidazolidine-5-carbonyl-L-histidyl-L-proline amide | 0.1 | 1 |
| 7 | L-pyroglutamyl-N$^{3im}$-carboxymethyl-L-histidyl-L-proline amide | 0.1 | 1 |
| 8 | D-2-ketopiperidine-6-carbonyl-L-histidyl-L-proline amide | 0.1 | 0.25 |
| 9 | L-2-ketopiperidine-6-carbonyl-L-histidyl-L-2-piperidinecarboxylic acid methyl ester | 0.016 | 1 |
| 10 | L-pyroglutamyl-D,L-histidyl-D,L-2-piperidinecarboxylic acid methyl ester | S.N. | 0.5 |
| 11 | L-pyroglutamyl-D,L-histidyl-L-2-piperidinecarboxylic acid methyl ester | S.N. | 1 |
| 12 | L-pyroglutamyl-L-histidyl-L-2-piperidinecarboxamide | 1 | 1 |
| 13 | D,L-2-ketopiperidine-6-carbonyl-L-histidyl-L-proline methyl ester | 0.02 | S.N. |
| 14 | L-2-ketoimidazolidine-5-carbonyl-L-histidyl-L-proline methyl ester | 0.001 | S.N. |
| 15 | L-2-ketooxazolidine-4-carbonyl*-L-histidyl-L-proline amide | 0.001 | S.N. |
| 16 | 2-pyrrolecarbonyl**-L-histidyl-L-proline amide | 0.001 | S.N. |

*2-ketooxazolidine-4-carboxylic acid has the formula

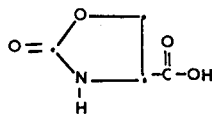

TABLE I-continued
THYROTROPIN RELEASING HORMONE AND ANTI-DEPRESSANT ACTIVITIES
| No | Peptide | TS | AD |
|---|---|---|---|

**2-pyrrolecarboxylic acid has the formula

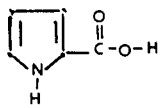

The data in Table I clearly illustrates the pharmacological effectiveness and unexpected separation of TS and AD activities of the present peptides.

Based on the in vivo effectiveness of the present peptides as thyrotropin releasing activators and as central nervous system stimulants (anti-depressant activity), these peptides may be effectively used for treating mammals suffering from central nervous system depression and/or in need of thyrotropin release activation.

The peptides can be administered by any convenient method, e.g. orally, parenterally, intravenously, sublingually, by insulation, by suppository and the like.

Dosage levels adequate to produce the desired effect are used. Generally, the dosage range will be from 0.05 to 100 mg. per dose depending on the method of administration. Dosage intervals will depend on the extent of relief desired. The tripeptides can be administered along, in pharmaceutically acceptable carriers or in formulations with other pharmaceutically active substances, as desired.

Claims to the invention follow.
What is claimed is:
1. Tripeptide having the formula

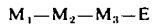

wherein
a. $M_1$ is selected from the group consisting of 2-ketoimidazolidine-5-carboxylic acid, 2-ketopiperidine-6-carboxylic acid, and pyroglutamic acid,
b. $M_2$ is selected from the group consisting of histidine and $N^{3im}$-substituted-histidine wherein the substituent is $C_1$-$C_6$ lower alkyl or —(CH$_2$)$_b$COOH, where $b$ is an integer from 1–4,
c. $M_3$ is selected from the group consisting of L-2-piperidinecarboxylic acid, L-proline and L-thiazolidine-5-carboxylic acid, and
d. E is selected from the group consisting of —NH$_2$ and -OR wherein R is $C_1$-$C_{10}$ alkyl, such that (i) when E is —NH$_2$, pyroglutamic acid and L-proline do not occur together in said tripeptide, and (ii) when E is —OR , histidine and L-proline do not occur together in said tripeptide.
2. Tripeptide of claim 1 wherein E is —NH$_2$.
3. Tripeptide of claim 2 wherein $M_1$ is 2-ketopiperidine-6-carboxylic acid.
4. Tripeptide of claim 2 wherein $M_1$ is L-2-ketopiperidine-6-carboxylic acid.
5. Tripeptide of claim 4 wherein $M_2$ is L-histidine.
6. Tripeptide of claim 5 wherein $M_3$ is L-proline.
7. Tripeptide of claim 5 wherein $M_3$ is L-2-piperidinecarboxylic acid.
8. Tripeptide of claim 5 wherein $M_3$ is L-thiazolidine-5-carboxylic acid.
9. Tripeptide of claim 2 wherein $M_1$ is 2-ketoimidazolidine-5-carboxylic acid.
10. Tripeptide of claim 2 wherein $M_1$ is pyroglutamic acid.
11. Tripeptide of claim 2 wherein $M_1$ is L-pyroglutamic acid.
12. Tripeptide of claim 11 wherein $M_2$ is L-histidine.
13. Tripeptide of claim 12 wherein $M_3$ is L-2-piperidinecarboxylic acid.
14. Tripeptide of claim 12 wherein $M_3$ is L-thiazolidine-5-carboxylic acid.
15. Tripeptide of claim 2 wherein $M_3$ is L-2-piperidinecarboxylic acid.
16. Tripeptide of claim 2 wherein $M_2$ is $N^{3im}$-substituted-L-histidine wherein the substituting groups are selected from the lower alkyl and —(CH$_2$)$_b$—COOH, $b$ being an integer of from 1–4.
17. Tripeptide of claim 16 wherein $M_2$ is $N^{3im}$-CH$_3$-L-histidine.
18. Tripeptide of claim 16 wherein $M_2$ is $N^{3im}$—CH$_2$—COOH-L-histidine.
19. Tripeptide having the formula: Pyroglutamic acid -$N^{3im}$—(CH$_2$)$_b$—COOH-L-histidine-L-proline-NH$_2$ wherein $b$ is an integer of from 1–4.
20. Tripeptide of claim 19 wherein $b$ is 1.
21. Tripeptide of claim 20 wherein said pyroglutamic acid is L-pyroglutamic acid.
22. Tripeptide of claim 1 wherein E is —OR.
23. Tripeptide of claim 22 wherein $M_1$ is pyroglutamic acid.
24. Tripeptide of claim 22 wherein $M_1$ is L-pyroglutamic acid.
25. Tripeptide of claim 24 wherein $M_2$ is L-histidine.
26. Tripeptide of claim 25 wherein $M_3$ is L-2-piperidinecarboxylic acid.
27. Tripeptide of claim 25 wherein $M_3$ is L-thiazolidine-5-carboxylic acid.
28. Tripeptide of claim 26 wherein R is —CH$_3$.
29. Tripeptide of claim 27 wherein R is —CH$_3$.
30. Tripeptide of claim 22 wherein $M_1$ is 2-ketoimidazolidine-5-carboxylic acid.
31. Tripeptide of claim 22 wherein $M_1$ is L-2-ketoimidazolidine-5-carboxylic acid.
32. Tripeptide of claim 31 wherein $M_2$ is L-histidine.
33. Tripeptide of claim 32 wherein $M_3$ is L-2-piperidinecarboxylic acid.
34. Tripeptide of claim 33 wherein R is —CH$_3$.
35. Tripeptide of claim 32 wherein $M_3$ is L-thiazolidine-5-carboxylic acid.
36. Tripeptide of claim 35 wherein R is —CH$_3$.
37. Tripeptide of claim 22 wherein $M_1$ is 2-ketopiperidine-6-carboxylic acid.
38. Tripeptide of claim 22 wherein $M_1$ is L-2-ketopiperidine-6-carboxylic acid.
39. Tripeptide of claim 38 wherein $M_2$ is L-histidine.
40. Tripeptide of claim 39 wherein $M_3$ is L-2-piperidinecarboxylic acid.
41. tripeptide of claim 40 wherein R is —CH$_3$.
42. Tripeptide of claim 39 wherein $M_3$ is L-thiazolidine-5-carboxylic acid.

43. Tripeptide of claim 42 wherein R is —$CH_3$.

44. Tripeptide of claim 22 wherein $M_3$ is L-2-piperidinecarboxylic acid.

45. Tripeptide of claim 22 wherein $M_2$ is $N^{3im}$ substituted-L- histidine wherein the substituting groups are selected from lower alkyl and —$(CH_2)_b$—COOH, $b$ being an integer of from 1-4.

46. Tripeptide of claim 45 wherein $M_2$ is $N^{3im}$-$CH_3$-L-histidine.

47. Tripeptide of claim 45 wherein $M_2$ is $N^{3im}$—$CH_2$—COOH-L-histidine.

48. Tripeptide having the formula L-pyroglutamic acid-$N^{3im}$ substituted-L-histidine-L-proline-OR wherein the substituting groups are selected from lower alkyl and $(CH_2)_b$—COOH, $b$ being an integer of from 1-4 and R is $C_1$-$C_{10}$ alkyl.

49. Tripeptide of claim 48 wherein said substituting group is —$CH_3$.

50. Tripeptide of claim 49 wherein R is —$CH_3$.

51. Tripeptide of claim 48 wherein said substituting group is —$CH_2$—COOH.

52. Tripeptide of claim 49 wherein R is —$CH_3$.

53. Tripeptide of claim 18 wherein $M_1$ is L-2-ketopiperidine-6-carboxylic acid and $M_3$ is L-thiazolidine-5-carboxylic acid.

* * * * *

UNITED STATES PATENT OFFICE
CERTIFICATE OF CORRECTION

PATENT NO. : 3,959,248
DATED : May 25, 1976
INVENTOR(S) : Daniel F. Veber, Frederick W. Holly, Ruth F. Nutt, and Sandor L. Varga It is certified that error appears in the above-identified patent and that said Letters Patent are hereby corrected as shown below:

```
Column 1, penultimate line; Column 11, line 63;
Column 12, lines 4, 16 and 17; Columns 3 and 4, Table 1,
Compounds 1 and 4; Column 15, lines 49 and 66;
Column 16, lines 19, 45, 57 and 68; and
Column 18, line 12;    "5" should read -- 4 -- .
```

Signed and Sealed this

Fifteenth Day of February 1977

[SEAL]

Attest:

RUTH C. MASON
*Attesting Officer*

C. MARSHALL DANN
*Commissioner of Patents and Trademarks*